United States Patent [19]
Ito et al.

[11] Patent Number: 5,349,951
[45] Date of Patent: Sep. 27, 1994

[54] OPTICAL CT IMAGING DEVICE

[75] Inventors: Yoshitoshi Ito, Ome; Fumio Kawaguchi, Hinode; Yukito Shinohara, Tokyo; Munetaka Haida, Isehara, all of Japan

[73] Assignees: Hitachi, Ltd.; Tokai University, both of Tokyo, Japan

[21] Appl. No.: 35,117

[22] Filed: Mar. 19, 1993

[30] Foreign Application Priority Data

Mar. 19, 1992 [JP] Japan .................................. 4-063055

[51] Int. Cl.$^5$ .............................................. A61B 6/03
[52] U.S. Cl. ................................. 128/633; 128/664;
            128/665; 128/666; 250/339.06; 250/358.1
[58] Field of Search ............... 128/664, 665, 633, 666,
                                    128/634; 250/339, 341, 358.1

[56] References Cited
U.S. PATENT DOCUMENTS

| | | | |
|---|---|---|---|
| 4,515,165 | 5/1985 | Carroll | 128/665 |
| 4,910,404 | 3/1990 | Cho et al. | 128/633 |
| 5,039,856 | 8/1991 | Tron | 250/358.1 |
| 5,088,493 | 2/1992 | Giannini et al. | 128/664 |
| 5,148,022 | 9/1992 | Kawaguchi et al. | 250/341 |

*Primary Examiner*—Ruth S. Smith
*Attorney, Agent, or Firm*—Antonelli, Terry Stout & Kraus

[57] ABSTRACT

A device for measuring the inside information of a light-scattering specimen using a Line Spread Function (LSF) function of a light-scattering specimen and the intensity distribution of light which is transmitted through the light scattering specimen in repeating light scattering and output from the light scattering specimen. The device comprises: an optical system for illumination for irradiating a specimen to be measured (a light scattering specimen); an optical system for detection for detecting the transmitted light through the specimen; and a data processor for operating the detected transmitted light data. The above-mentioned data processor operates the inside information of a specimen to be measured based on the light intensity distribution of the transmitted light through the specimen and an LSF function which is newly defined, and displays the inside information as a tomograph image.

16 Claims, 4 Drawing Sheets

OPTICAL CT IMAGING DEVICE

BACKGROUND OF THE INVENTION

The present invention relates to a method for measuring the light absorption coefficient of a light scattering material and the device of the same and further it relates to a diagnostic imaging device (optical CT imaging device) utilizing the method.

For the observation of a tomograph image in a human body, an X-ray CT method is widely used. Since a state inside a human body can be known without performing an operation for an observation object (human body) by using an X-ray CT device, it is widely used for diagnostic purposes. On the other hand, a problem of lesion by radiation of X-rays on a human body cannot be neglected. The development of an optical CT imaging device in which rays of light is used in place of X-rays is suggested as a method for solving the problem. In order to realize an optical CT device, it is necessary to measure the information inside a human body with rays of light. There are papers as shown below as the examples in which the measurement of the information inside a human body is attempted with rays of light.

In 1977, a measurement of a physiological change which occurred in a human head based on the change in the transmitted light intensity by irradiating the head of an adult with infrared rays was attempted by F. F. Jöbsis. This was the first attempt on the measurement of change in light absorption quantity corresponding to the physiological change inside a head, and the details are described in a Japanese Kokai No. 115232/82. In the gazette, there is a comment on the constitution of an optical CT imaging device utilizing the above-mentioned measurement method, but the idea is based on a simple idea of substituting a light beam for X-rays in an X-ray CT imaging device.

Another measurement device for measuring the information inside a human body with a light beam is shown in a Japanese Kokai No. 163634/90. In the device, a light-scattering substance is irradiated by a light beam, and the reflected light which comes in the vicinity of the light incident point is detected for the measurement of the information inside a human body.

There is a further paper than the above described papers, reporting that an optical CT image is obtained by measuring light absorption characteristics of a light-scattering substance with a faint light measurement method called a light heterodyne method (Toida et al, "Measurement of a Faint Signal Light Buried in Scattered Light", BME Journal, Vol. 4 (1990), pp 1223). In a case where a transmitted light through a light-scattering substance is measured by a light heterodyne method, the intensity of the transmitted light becomes very weak, so that this method cannot be applied to a thick specimen.

SUMMARY OF THE INVENTION

An object of the present invention is to realize an optical CT device which is able to calculate the projection data of a specimen from the intensity distribution of a scattered and transmitted light beam for irradiating the specimen (light scattering substance) and to obtain a tomograph image of the specimen based on the back-projection method using the calculated data.

DESCRIPTION OF THE PREFERRED EMBODIMENTS

Figure 1:
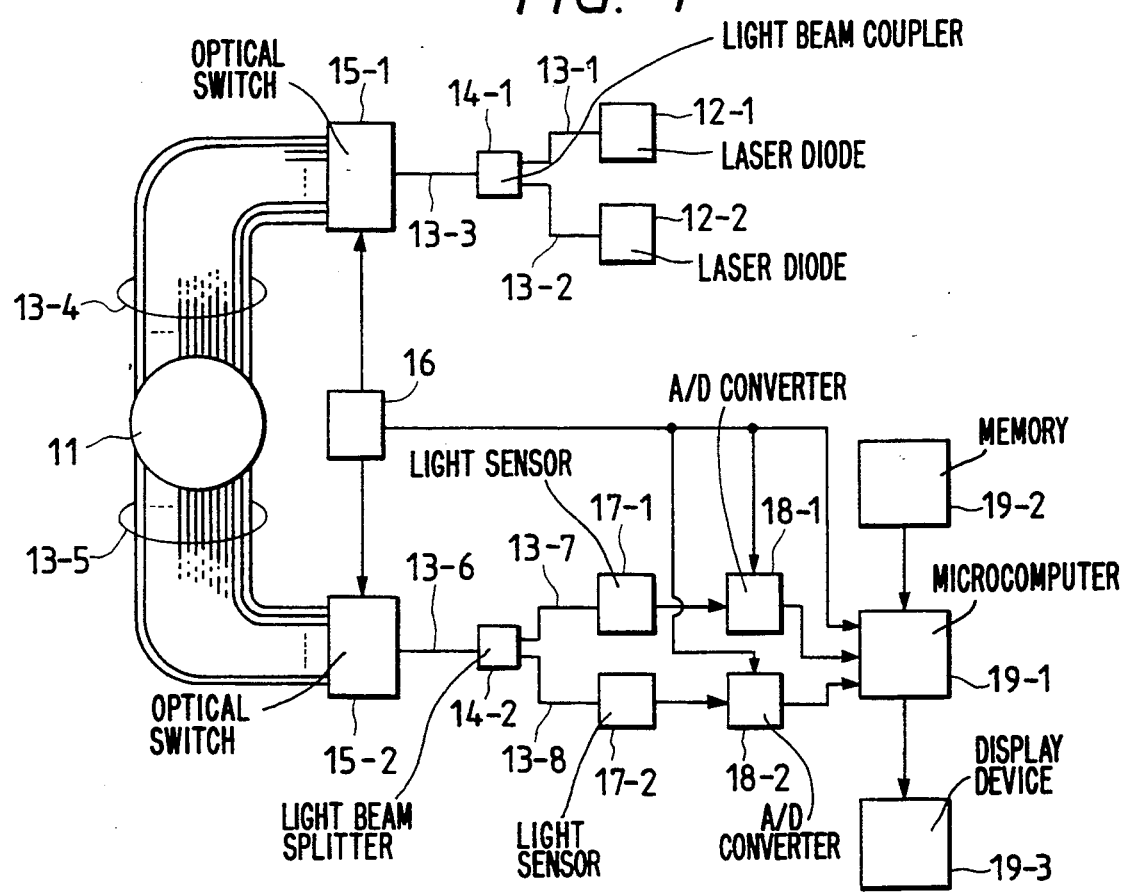
FIG. 1 is a basic constitution of an optical CT device being an embodiment according to the present invention.

The embodiments according to the present invention will be explained in detail referring to the drawings in the following.

Figure 2:
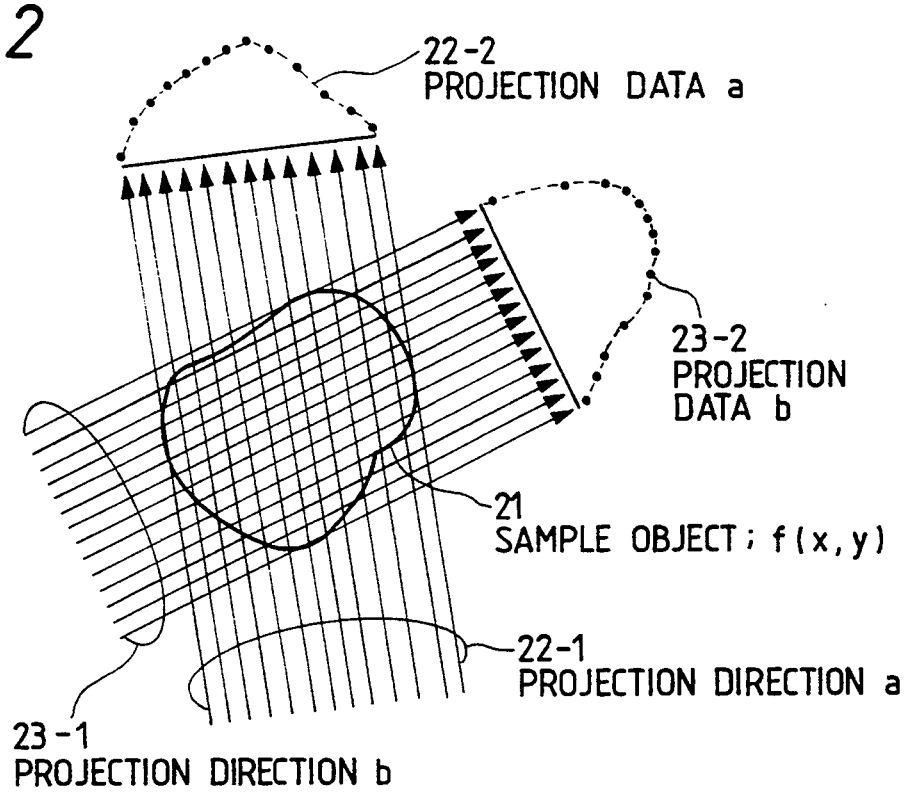
FIG. 2 is an illustrative representation of a back-projection method.

In general, in an X-ray tomography device, a well known method as a back projection method is used as a constituting method of a tomograph image. In the method, the data called "projection" are utilized. Assuming that a two dimensional characteristic function of a specimen is expressed by a function $f(x,y)$, when the specimen is looked at from a certain direction, the $f(x,y)$ can be integrated along a straight line penetrating the specimen as shown in FIG. 2. The integral value is decided according to the position of the straight line, an integral path, so that a series of integral values corresponding to the positions of the straight lines in one direction can be obtained. The series of integral values are the data called projection.

In FIG. 2, a numeral 21 indicates a specimen of which a tomograph image is to be obtained. A reference numeral 22-1 is a straight line penetrating the specimen 21 in a certain direction ("a" direction). A reference numeral 22-2 expresses a series of integral values which are obtained by integrating the $f(x,y)$ along straight lines in an "a" direction, that is, the projection data "a". A reference numeral 23-1 is a straight line penetrating the specimen 21 in a different direction ("b" direction), and 23-2 expresses the projection data "b" obtained by integrating $f(x,y)$ along a series of straight lines 23-1.

The projection data as described in the above are measured in a plurality of directions, and a method of finding the value of $f(x,y)$, the characteristic distribution inside the specimen, from the measured data by operation is a so called back-projection method.

In order to use the above-mentioned back-projection method, integral values of a characteristic function taking straight lines penetrating the specimen as integral paths are needed. In the case of an X-ray CT imaging device, X-rays transmit through a specimen straight, so that accurate projection data can be measured. Even if projection data are intended to measure with a light beam, if a specimen is a light-scattering substance like a human body, the light beam cannot transmit through the specimen straight, so that accurate projection data cannot be measured. Because of this, if simply a light beam is considered to be a substitute for X-rays in an X-ray CT imaging device, a tomograph image of a light-scattering substance, for example a human body, cannot be realized.

In the present invention, the characteristic of a light-scattering specimen is expressed with a newly introduced function called a "Line Spread Function" (hereinafter referred to as LSF function). The LSF function expresses the rate of divergence of a light beam scattered in a light-scattering specimen when the light beam incident on the specimen transmits through it.

For example, an incident point of a light beam which penetrates into a light-scattering specimen is put as Pi and the output point of the light beam is put as Po when the light beam is assumed to be transmitted through a specimen in a straight line. An incident light beam on the specimen is transmitted in the specimen in being diverged by scattering and only a small part of the whole light beam is output from the point Po. In this case, only the light which is input at Pi and output from Po is paid attention. In the light output from the point Po, there are included not only the light input at the point Pi and transmitted straight to the point Po but also the light which is once separated from the straight line path by scattering, passed partially through the neighboring paths and returned to the point Po by scattering. In this case, a straight line path between the point Pi and the point Po, and the neighboring paths being parallel to the straight line path are considered, then while the incident light beam is transmitted through the specimen, the rate of passing the straight line path and the rate of passing each of the neighboring paths can be considered. The LSF function is the one in which the rate of passing each of the neighboring paths of the scattered transmitted light is expressed as a function of the distance to the path from the straight line path from Pi to Po. An average value of light absorption in a straight line path set in a light-scattering specimen can be calculated using the LSF function and the measurement values of transmissivity of the scattered light; thereby, it is made possible to obtain a tomograph image of a light-scattering specimen by using the above-mentioned calculated values.

Figure 3:
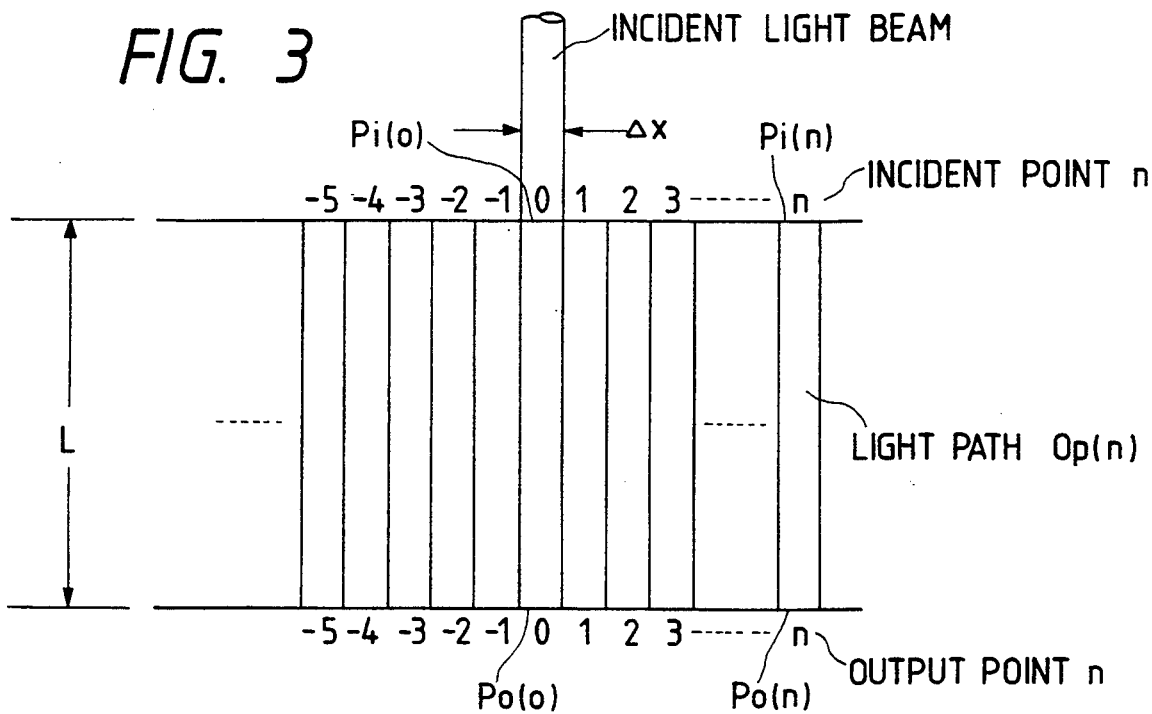
FIG. 3 is an illustrative representation about an incident point of light on a light scattering specimen, a light path in the specimen and an output point of light from the specimen.

A method of measuring a light absorption coefficient in a specimen by using the LSF function which expresses the characteristic of a light-scattering specimen will be explained. The scattering of a light beam in a substance is described in three-dimensional expressions, but in this place, the explanation will be given using two-dimensional drawings for simplifying the explanation. At first, a case will be considered where fine parallel light beams having a width of $\Delta x$ is input to a specimen having constant thickness L as shown in FIG. 3 in a direction perpendicular to the incident plane. It is assumed that the specimen is divided into strips of $\Delta x$ wide and they are numbered with n, and respective incident points are expressed by $Pi_{(n)}$ using the numbers. When the specimen is transparent, an incident light beam which is input at the point $Pi_{(n)}$ is transmitted straight in the specimen. A light path along which the incident light beam input from the incident point $Pi_{(n)}$ is transmitted straight will be expressed as $Op_{(n)}$, and the output point of light which passed the light path will be expressed as $Po_{(n)}$. If a scattering cause is contained in the transparent specimen, the light beam is diverged by scattering with the proceeding and at the back of the specimen (output plane) the beam diameter becomes larger. Various kinds of scattering causes can be considered such as fine particles or reflection at an interface between parts having different refraction indexes. These scattering causes are distributed at random when a specimen is locally observed, but when it is observed as a whole they can be regarded as if they are uniformly distributed.

Now, a light beam which passed in a light scattering specimen having no light absorption will be considered. When a light beam of intensity Ii is input from an incident point $Pi_{(n)}$, the intensity Ios of the light which reaches an output point $Po_{(o)}$ can be expressed by equation (1) as $$Ios = Ii \cdot exp(-S \cdot L) \quad (1)$$

where S is a light scattering coefficient, L is the thickness of the specimen.

Light beams which reach the output point $Po_{(o)}$ do not pass the same path; it will be natural to think that an input light beam is branched into many light beams, and the respective branched light beams reach the output point $Po_{(o)}$ through different paths. It is considered that an incident light beam input to a specimen is composed of many basic light beams and these basic light beams are diverged by scattering and spread out. In other words, a light beam composed of many basic light beams being bundled to a light beam enters a specimen, and at the beginning it passed in a specimen along a light path $Op_{(o)}$ corresponding to the incident point $Pi_{(o)}$. Every time when the light beam meets a scattering cause, some of the basic light beams composing the light beam are scattered and change their paths. In repeating the path changes by scattering, the basic light beams which are bundled to a light beam at the beginning are separated and diverged, and reach the back of the specimen (output plane).

Figure 4:
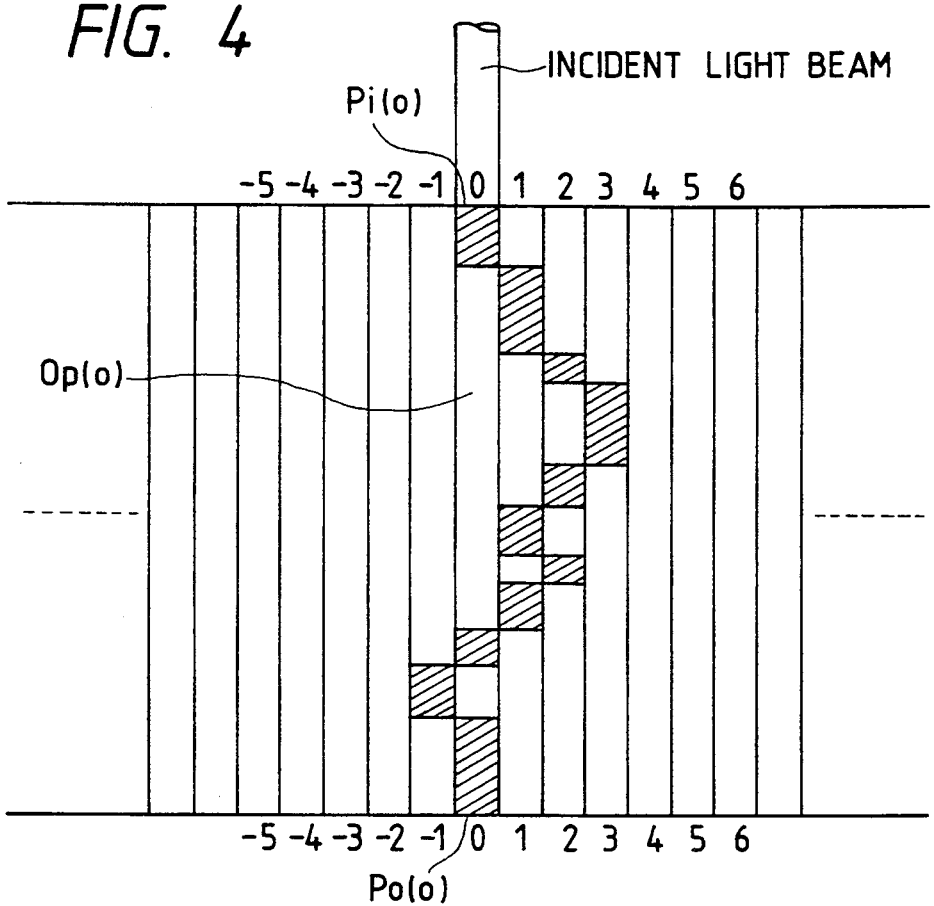
FIG. 4 is an illustrative representation for explaining a state of changing paths of a light beam which is transmitted while being scattered through a light scattering specimen.

Next, out of the basic light beams which are input to the specimen at the incident point $Pi_{(o)}$ and reach the back of the specimen, only those which reach the output point $Po_{(o)}$ will be considered and such a basic light beam will be expressed with Bm. The m is the number of each basic light beam. A scattering state of one of these basic light beams is typically shown in FIG. 4. As seen from FIG. 4, a light beam which is input to a specimen, at the beginning, passed in the light path $Op_{(o)}$. Every time the light beam meets a scattering cause the basic light beams repeat the changes of paths as described in the above and reach the output point $Po_{(o)}$. The basic beam Bm passed various light paths from the input to a specimen till it reaches the output point; the path length when the Bm passed nth optical path $Op_{(n)}$ is put as $\Delta Lnm$. The value of the $\Delta Lnm$ and the value of depth of the path from the specimen surface are decided by multiple scattering of the input light beam, so that they differ by basic beams, and the values vary irregularly.

Next, the case where a light-scattering specimen is a light absorbent substance will be considered. In this case, the state of scattering of a light beam is similar to the above-mentioned cases, but the intensity of a light beam which reaches the output point $Po_{(o)}$ is attenuated by light absorption. For example, the local average light absorption coefficient of a part (depth from the surface: l) on a light path $Op_{(n)}$ through which a basic light beam Bm passed while it is transmitted through the specimen is put as A(n,l), the light intensity of the basic light beam Bm when it is input at the input point $Pi_{(o)}$ is put as Iim, and the light intensity of the basic beam when it is output from the output point $Po_{(o)}$ is put as Iom; then Iom can be expressed by equation (2) shown below as $$Iom = Iim \cdot \exp\left[-\sum_n (A(n, 1) \cdot \Delta Lnm)\right] \quad (2)$$

The light intensity Io of the light which is output from the output point $Po_{(o)}$ on the light path $Op_{(o)}$ is the sum of the light intensity Iom of each basic light beam, so that it can be expressed by equation (3) as $$Io = \sum_m Iom = \sum_m \left\{ Iim \cdot \exp\left[-\sum_n (A(n, 1) \cdot \Delta Lnm)\right] \right\} \quad (3)$$

When the value of the absorption coefficient A(n,1) is small, equation (3) can be approximated by equation (4) shown below as $$\begin{aligned} Io &= \sum_m \left\{ Iim \cdot \left[1 - \sum_n (A(n, 1) \cdot \Delta Lnm)\right]\right\} \\ &= \sum_m I_i m - \sum_n \sum_m [Iim \cdot A(n, 1) \cdot \Delta Lnm] \end{aligned} \quad (4)$$

The first term on the right side in the second line in equation (4) is the intensity of the scattered transmitted light when there is no light absorption, so that the value is Ios. The second term on the right side has a meaning as shown in the following: the product of the light intensity Iim of each basic light beam which passed each light path, the length of the part of a light path, $\Delta Lnm$, through which each basic light beam passed, and the light absorption coefficient A(n,1) of the part of the light path through which each basic light beam passed will be found; the sum of the above described products concerning all basic light beams which are passed through respective paths will be found; and then the total sum of the above-mentioned sum concerning the total light paths will be found.

Figure 5:
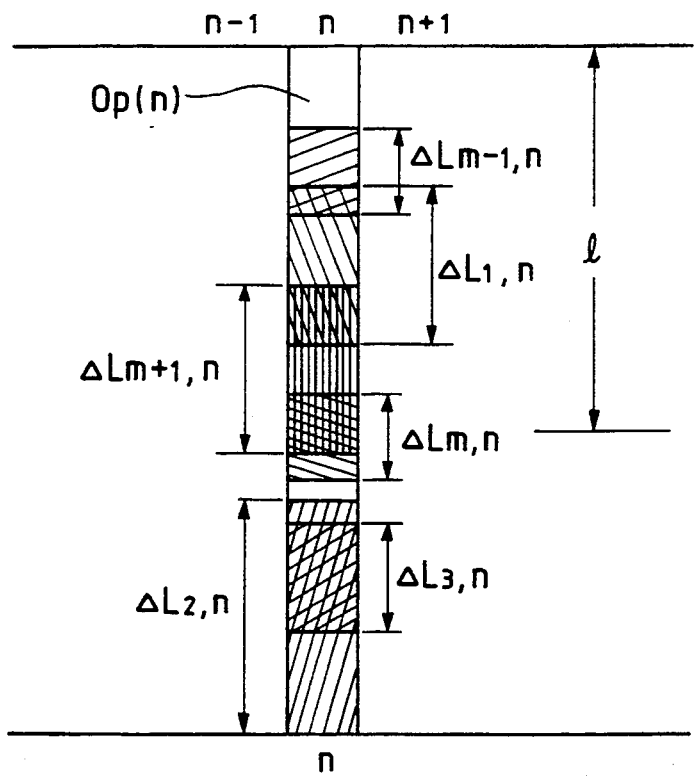
FIG. 5 is an illustrative representation showing a state of each light beam which passed through an arbitrary light path.

In FIG. 5, there is shown a state where a plurality of basic light beams are passed an arbitrary light path $Op_{(n)}$ with different pass lengths by respective basic light beams. In the figure, for example, $\Delta Lmn$ shows that a number m basic light beam in Bm passed a partial light path having a length of $\Delta Lmn$ which is positioned at a depth of 1 from the specimen surface in the nth path $Op_{(n)}$. The depth 1 of each partial light path through which a basic light beam passed is different by light beams as described in the above, and the value is found to be irregular. Therefore, the light absorption coefficient A(n,1) in each partial light path through which each basic light beam passed is different by light beams. The value of the light absorption coefficient A(n,1), the light intensity Iim of each basic light beam, and the transmitted path length $\Delta Lnm$ are decided by scattering, so that it is considered that there is no correlation among them. Because of this, when the sum of many terms is to be found as in the equation (4), the average light absorption coefficient $Aav_{(n)}$ concerning each light path $Op_{(n)}$ can be substituted, in approximation, for the light absorption coefficient A(n,1) of passed parts of respective basic light beams. The average light absorption coefficient $Aav_{(n)}$ of each light path is expressed by equation (5) shown below as $$Aav_{(n)} = (1/L) \cdot \int_0^L A(n, 1) dl \quad (5)$$

Therefore, equation (4) can be expressed by equation (6) shown below as $$Io = Ios - \sum_n \left( Aav_{(n)} \cdot L_{(n)} \cdot Ios \cdot \sum_m [Iim \cdot \Delta Lnm/(Ios \cdot L_{(n)})] \right) \quad (6)$$

A part of equation (6) will be expressed as $$\sum_m [Iim \cdot \Delta Lnm/(Ios \cdot L_{(n)})] = LSF_{(n)} \quad (7)$$

The function $LSF_{(n)}$ described in the above has a form of a fractional expression, and the numerator is the total sum, concerning total basic light beams, of the product of the light intensity Iim of each light beam which passes nth light path $Op_{(n)}$ from the input point $Pi_{(o)}$ and the passed path length $\Delta Lnm$, and the denominator is for normalizing the numerator. The value of equation (7) expresses the ratio of the intensity of the light which reaches the output point in passing through the specimen when there is no light absorption to the intensity of the scattering light which reaches the output point passing through respective light paths. Therefore, the function $LSF_{(n)}$ is a function which reflects the diffusion of light caused by scattering.

The scattering causes in a light scattering specimen can be regarded to be uniformly distributed, so that the light in the specimen diffuses symmetrically with respect to the incident point. Because of this, the intensity of light which passes the light path $Op_{(n)}$ and the intensity of light which passes the light path $Op_{(-n)}$ are equal where both light paths are disposed in the same distance from the incident point; thereby equation (8) holds good shown below as $$LSF_{(n)} = LSF_{(-n)} \quad (8)$$

the equation shows that the function is an even function.

Equation (6) can be transformed to equation (9) by using the function LSF shown below as $$Io = Ios - \sum_n \{Aav_{(n)} \cdot L_{(n)} \cdot Ios \cdot LSF_{(n)}\} \quad (9)$$

In the above explanation, the incident point of a light beam is shown as $Pi_{(o)}$, but when the incident point is assumed to be an arbitrary point $Pi_{(n')}$, the transmitted light intensity $Io_{(n')}$ at the output point $Po_{(n')}$ is expressed by equation (10) shown below as $$Io_{(n')} = Ios - \sum_n \{Aav_{(n)} \cdot L_{(n)} \cdot Ios \cdot LSF_{(n-n')}\} \quad (10)$$

Next, a case where two kinds of light having the same intensity and different wave lengths, $\lambda_1$, $\lambda_2$ are input at the incident point $Pi_{(n')}$ will be considered. The intensity of transmitted light of each wave length is given by equation (9). Further the difference in light intensity between the two kinds of transmitted light, $\Delta IO_{(n')}$ can be found in equation (11) shown below as $$\Delta I o_{(n')} = - \sum_n \{[Aav_{\lambda 1(n)} - Aav_{\lambda 2(n)}] \cdot L_{(n)} \cdot Ios \cdot LOS_{(n-n')}\} \quad (11)$$

$$= - \sum_n \{\Delta Aav_{(n)} \cdot L_{(n)} \cdot Ios \cdot LSF_{(n-n')}\}$$

In this case, $\Delta Aav_{(n)}$ shows the difference between average light absorption coefficients for the light of wavelength $\lambda_1$ and for the light of wavelength $\lambda_2$ in the light path $Op_{(n)}$.

Since there is little wavelength dependence in the state of light scattering in a light scattering specimen, when the difference between two wavelengths is small, the $LSF_{(n)}$ in each wavelength is regarded to have approximately the same value. In this case also, the values of $LSF_{(n)}$ for the light of wavelength $\lambda_1$ and for the light of wavelength $\lambda_2$ are regarded to be equal.

As described above, the relations among the transmitted light intensity difference $\Delta Io_{(n)}$ between two light beams of different wavelengths, the average light absorption coefficient $Aav_{(n)}$, the light scattering coefficient S, the $LSF_{(n)}$ function, and the thickness of the light scattering specimen $L_{(n)}$ are given by equation (11). In the present invention, the $\Delta Io_{(n)}$, the light scattering coefficient S and the thickness of the light scattering specimen $L_{(n)}$ are found by measurement, and the value of the function $LSF_{(n)}$ is found by a simulation method such as a Monte Carlo method or by an experiment, etc. and these values are substituted for respective symbols in equation (11), and the difference in average light absorption coefficient in each light path caused by the difference in wavelength, $\Delta Aav_{(n)}$, is found by operation.

Fourier transformation is utilized in order to actually obtain the value of $\Delta Aav_{(n)}$ using equation (11) described in the above. When both sides of equation (11) are Fourier-transformed, the right side of the equation has a form of convolutions of the $LSF_{(n)}$ function and the $\Delta Aav_{(n)} \cdot L_{(n)}$, so that the Fourier transformation of the right side of equation (11) is given as a product of the Fourier transformation of the $LSF_{(n)}$ function and the Fourier transformation of the $\Delta Aav_{(n)} \cdot L_{(n)}$. When the Fourier transformation is expressed by a symbol $F\{\ \}$, equation (12) can be obtained as $$F\{\Delta Io_{(n)}/Ios\} = -F\{\Delta Aav_{(n)} \cdot L_{(n)}\} \cdot F\{LSF_{(n)}\} \quad (12)$$

Further equation (12) can be transformed to equation (13) shown below as $$F\{\Delta Aav_{(n)} \cdot L_{(n)}\} = -F\{\Delta Io_{(n)}/Ios\}/F\{LSF_{(n)}\} \quad (13)$$

thus Fourier transformation of $Aav_{(n)}L_{(n)}$ can be obtained.

The average light absorption coefficient $Aav_{(n)} \cdot L_{(n)}$ of each light path can be obtained by operating the inverse Fourier transformation of equation (13). The value of $L_{(n)}$ in equation (13) can be measured from the form of a specimen; thereby, from the value obtained by inverse Fourier transformation of equation (13), the average light absorption coefficient of each light path can be obtained.

It is intended in the present invention to obtain a tomograph image of a light scattering specimen by the above-mentioned back-projection method using the value of the average light absorption coefficient in each light path in a light scattering specimen which is obtained by the method as described in the above. The explanation of further details of the back-projection method is given in Gabor T. Herman "Image Reconstruction from Projections Academic Press, Copyright 1980)".

EMBODIMENT 1

FIG. 1 shows an embodiment according to the present invention. The present embodiment is related to a device for measuring blood distribution in a human body. The device is mainly composed of the following: an optical system for illumination for irradiating a living specimen with a light beam for measurement, an optical system for detection for detecting transmitted light through the living specimen, and a data processor for processing the detected transmitted light data.

In FIG. 1, a numeral 11 indicates a living specimen as an object of measurement. The optical system for illumination comprises: laser diodes 12-1 and 12-2 to be used as light sources, a light beam coupler 14-1, a light switch 15-1, and optical fibers 13-1 to 13-4 disposed between the laser diodes, 12-1 and 12-2, and the light beam coupler 14-1, between the light beam coupler 14-1 and the optical switch 15-1, and between the optical switch 15-1 and the living specimen 11 for the transmission of illumination light. The wavelengths of the output laser beams of laser diodes 12-1 and 12-2 can be in a range of 0.5 $\mu$m–0.9 $\mu$m, and for the present embodiment are respectively 0.57 $\mu$m and 0.70 $\mu$m.

The optical system for detection comprises: a light switch 15-2, a light beam splitter 14-2, light sensors 17-1 and 17-2, and optical fibers 13-5 to 13-8 for connecting the living specimen 11 and the light switch 15-2, the light switch 15-2 and the light beam coupler 14-2, and the light beam splitter 142 and the light sensors 17-1 and 17-2.

The optical fiber 13-4 on the illumination side and the optical fiber 13-5 on the detection side are constituted with a plurality of fiber elements being bundled, and the contact points with the living specimen 11 of optical fibers on both sides are constituted to face each other with the living specimen 11 in between. Each of the fiber elements of the optical fiber 13-4 on the illumination side and each of the fiber elements of the optical fiber 13-5 on the detection side are so disposed and constituted that the emitted light from the illumination end of a fiber element for irradiating the living specimen 11 is assumed to proceed in the living specimen 11 in a straight line and the detection end of a fiber element on the detection side is positioned on the optical axis of the hypothetical transmitting light.

The data processor comprises: AD converters 18-1 and 18-2, a microcomputer 19-1 for data processing, a memory device 19-2 connected to the microcomputer 19-1, and a display device 19-3 for displaying the processed data. A reference numeral 16 is a clock signal generator for operating the light switches, 15-1 and 15-2, in synchronization with each other.

Next, the operation of the present device will be explained. Laser beams output from the laser diodes, 12-1 and 12-2, are led to the light beam coupler 14-1 through respective optical fibers, 13-1 and 13-2, and both laser beams are synthesized (superposed) by the beam coupler 14-1. The synthesized laser beam is led to the light switch 15-1 through the optical fiber 13-3 and the laser beam is led into a fiber element selected from among a plurality of fiber elements which constitute the optical fiber 13-4 to be used for illumination by the light switch 15-1, and it irradiates the living specimen 11.

The laser beam for irradiating the living specimen 11 passed through the living specimen in repeating scattering in the living specimen, and is output to the detection side. The laser beam output from the living specimen 11 is input to the optical fiber 13-5 and is led to the light switch 15-2 through the optical fiber 13-5. The light switch 15-2 selects a fiber element which is in a position just opposing to the fiber element selected for irradiating the living specimen 11 with the laser beam from among a plurality of fiber elements constituting the optical fiber 13-5, and leads the detection light led by the fiber element to the light beam splitter 14-2 through the optical fiber 13-6.

The light beam splitter 14-2 separates the detection light input to it by wavelengths, and the light beam of 0.57 μm wavelength is sent to the light sensor 17-1 through the optical fiber 13-7, and the light beam of 0.70 μm wavelength is sent to the light sensor 17-2 through the optical fiber 13-8. The light sensors, 17-1 and 17-2, convert the intensity of detection light beams of respective wavelengths to electric signals and output them. The outputs of the light sensors, 17-1 and 17-2, are converted to digital signals by respective AD converters, 18-1 and 18-2, and the signals are sent to the microcomputer 19-1.

The switching of the light switches, 15-1 and 15-2, is performed in synchronization with each other by the same clock signal from the clock signal generator 16. In this case, the switching of the switches (switching for the selection of optical fiber elements) is performed in a manner that the position of a fiber element for irradiating the living specimen 11 selected by the light switch 15-1 and the position of a fiber element for inputting the output light from the living specimen 11 selected by the light switch 15-2 are positioned to correctly face each other in a straight line. As described above, the irradiating position of the irradiation light beam on the specimen 11 and the detecting position of detection light from the specimen 11 are both scanned in synchronization by performing synchronized switching of the light switch 15-1 and the light switch 15-2; thus, the measurement of light transmitted through a living specimen is performed.

As the outputs of the light sensors, 17-1 and 17-2, the transmitted light intensity through a living specimen of both light beams of 0.57 μm wavelength and of 0.70 μm wavelength, that is, the transmitted scattering light intensity $Io_{(n')}$ expressed in equation (10) can be obtained concerning respective wavelengths.

The microcomputer 19-1 takes in digitized light intensity signal of the transmitted light through a living specimen from the light sensors, 17-1 and 17-2, in synchronization with the clock signal from the clock signal generator. Then, the difference in the intensity between the 2 transmitted scattering light of wavelengths of 0.57 μm and 0.70 μm is processed.

Figure 6:
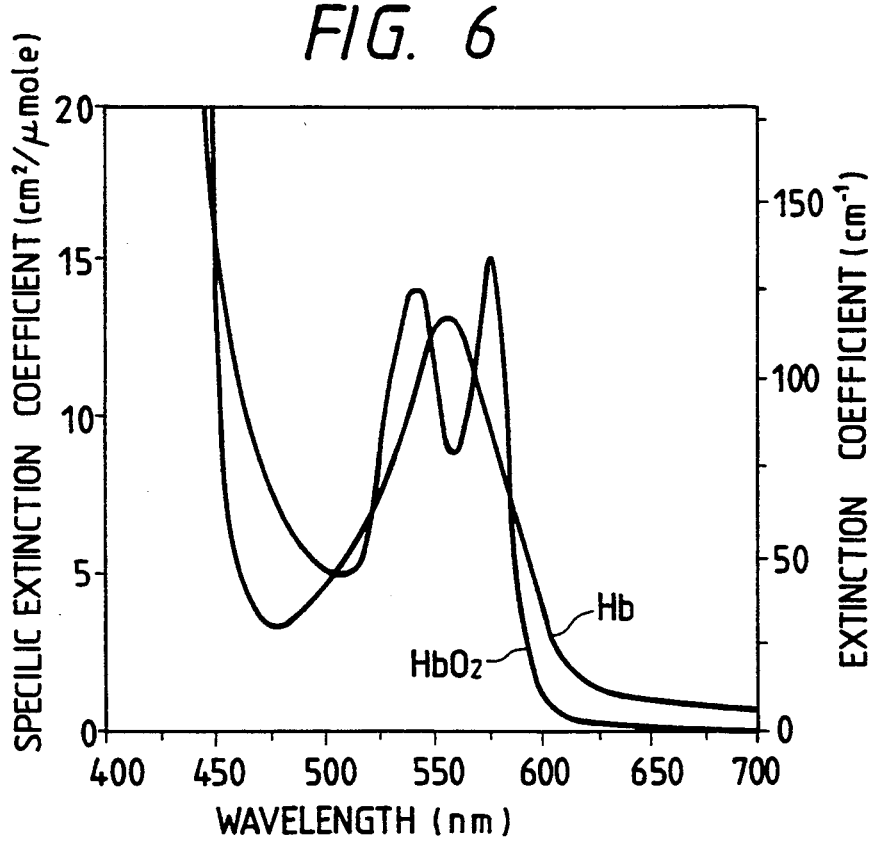
FIG. 6 is a chart showing the change in respiration coefficient caused by oxygenation of blood.

The absorption of light by blood in a living specimen generally varies according to the degree of oxygenation of blood. In FIG. 6, there is shown the change in absorption coefficient for the change in oxygenation of blood for each wavelength. As seen from the figure, at a wavelength of 0.57 μm, the light absorption coefficient shows a constant value independent of the degree of oxygenation of blood, so that the wavelength is a suitable wavelength for measuring the quantity of blood.

On the other hand, at a wavelength of 0.70 μm, the light absorption coefficient shows a very small value independent of the degree of oxygenation of blood, so that at the wavelength the change in light absorption coefficient by the change in quantity of blood is small and almost constant light absorption quantity is shown. Therefore, the difference in absorption quantity between these two wavelengths shows a value being proportional to the quantity of blood.

The value of the function $LSF_{(n)}$ concerning a living specimen 11 stored in the memory device 18 and the shape data of the living specimen 11, that is, the length $L_{(n)}$ of each light path $OP_{(n)}$ are substituted in equation (11), and the average absorption coefficient $Aav_{(n)}$ of each light path is processed.

At first, the $Aav_{(n)}$ in a direction decided by the optical fibers, 13-4 and 13-5 set for the living specimen 11 shown in FIG. 1 is calculated. Next, the attachment position and direction of the optical fibers for the living specimen 11 are changed, and the average light absorption coefficient in each light path in the different direction is measured in the same way. As described in the above, the average light absorption coefficients in each light path measured in a plurality of directions are obtained, and using these average light absorption coefficients a tomograph image of the living specimen 11 can be obtained by the back-projection method.

Figure 7:
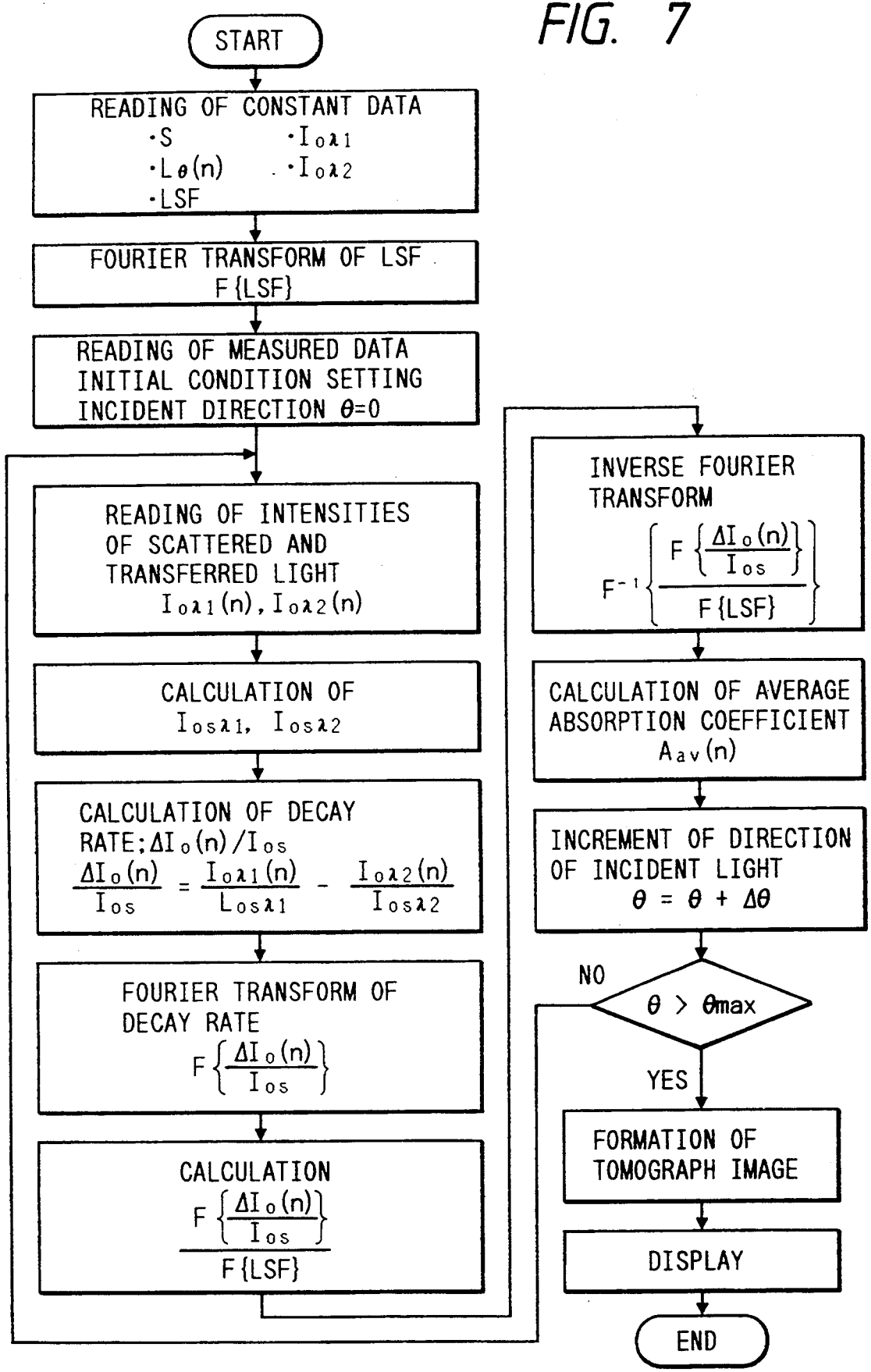
FIG. 7 is a flow chart showing the contents of the operation.

The process of operation expressed in the form of a flow chart is shown in FIG. 7.

The value of the average light absorption in each light path is proportional to blood quantity in the living specimen 11, so that the obtained tomograph image is an image in which the distribution of blood in the living specimen 11 is reflected.

EMBODIMENT 2

The present embodiment is related to an optical CT imaging device having a purpose of measuring the degree of oxygenation of blood in a living specimen. The constitution of the device is the same as shown in the embodiment 1. The different points between the present embodiment and the embodiment 1 is that a laser diode of 0.56 μm wavelength is used as the laser diode 12-2. The output wavelength of the laser diode 12-1 is 0.58 μm being similar to that in the embodiment 1. In the case of the embodiment 1, a laser beam of wavelength 0.70 μm is selected, of which the light absorption by blood of a living specimen is small and almost constant; in contrast to this, the laser beam of wavelength 0.56 μm is selected to be output from the laser diode 12-2 used in the present embodiment, of which the absorption coefficient is varied by the degree of oxygenation of blood as shown in FIG. 6. Therefore, the difference in average light absorption coefficient between the light beams of wavelengths of 0.56 μm and o.58 μm becomes a value in proportion to the oxygenation degree of blood; thereby, the oxygenation degree of blood can be found from the difference between the average light absorption values.

In the present embodiment, the difference in average light absorption coefficient between the light beams of 0.56 μm wavelength and of 0.58 μm wavelength is measured in each light path in the same way as described in the embodiment 1. The difference in average light absorption coefficient between two light beams takes a value dependent on the oxygenation degree of blood, and also the value varies in proportion to the quantity of blood contained in the light path. In order to cancel the change proportional to blood quantity, the ratio of the difference in average light absorption coefficient between the two light beams of the above-mentioned wavelengths to the average light absorption value about the light beam of 0.58 μm wavelength which varies in proportion to only blood quantity will be found. The value of the ratio is in proportion to the average light absorption value of a light beam of 0.56 μm wavelength for a constant blood quantity, so that the obtained value reflects only the oxygenation degree of blood. Of course the operation described in the above is processed by the microcomputer 19-1.

A tomograph image in a living specimen can be constituted using the values obtained in the operation as described in the above in the same method described in the embodiment 1. The tomograph image thus obtained is the one which expresses the distribution of oxygenation degree of blood.

In the present invention, light is utilized as a measurement probe; thereby there is an effect that the information inside a living specimen can be measured without giving any lesion to the living specimen.

What is claimed is:

1. A diagnostic device for obtaining an optical CT image of a living specimen, said device comprising:
   a light source generating a measuring light having at least a first wavelength component and a second wavelength component which is different from said first wavelength component;
   a first light guide including a plurality of first optical fibers guiding said measuring light to predetermined irradiating input points with respect to said living specimen;
   a first light scanner supplying said measuring light to respective said first optical fibers of said first light guide in a time-sequential scanning manner;
   a second light guide including a plurality of second optical fibers receiving light transmitted from said first light guide and through sadi living specimen at predetermined irradiating output points with respect to said living specimen;
   a second light scanner connected to said second light guide selecting a light output from respective said second optical fibers of said second light guide in a time-sequential scanning manner in synchronism with a time-sequence of said first light scanner;
   a light splitter splitting said light output into said first wavelength component and said second wavelength component;
   a light detector detecting an intensity of said first wavelength component and said second wavelength component; and
   a data processor obtaining a tomograph image of said living specimen by processing a distribution of differences in absorption quantity between said first wavelength component and said second wavelength component detected by said light detector using a line spread function which defines an inclusion ratio of light components transmitted through optical paths other than a straight path between said irradiating input points and said irradiating output points.

2. A diagnostic device as claimed in claim 1, in which said data processor obtains said tomograph image using said line spread function (LSF) as given by the following equation:

$$LSF_{(n)} = \sum_m [Iim \cdot \Delta Lnm/Ios \cdot L_{(n)}]$$

wherein
Iim is a light intensity of each basic light beam at an irradiating input point with respect to said living specimen;
ΔLnm is a path length when any basic light beam passes through any one of plural light paths parallel to said straight path between said irradiating input points and said irradiating output points;
Ios is a gross light intensity of basic light beams which reach said irradiating output points of said living specimen without absorption;
$L_{(n)}$ is a full path length of any of said plural light paths.

3. A diagnostic device as claimed in claim 2, in which a wavelength of said first wavelength component and said second wavelength component of said measuring light is in a range from 0.5 μm to 0.9 μm.

4. A diagnostic device as claimed in claim 3, in which said first light scanner and said second light scanner comprises a light switch.

5. A diagnostic device as claimed in claim 4, in which said light source comprises a semiconductor laser diode.

6. A diagnostic device as claimed in claim 3, in which said light source comprises a semiconductor laser diode.

7. A diagnostic device as claimed in claim 2, in which said light source comprises a semiconductor laser diode.

8. A diagnostic device as claimed in claim 2, in which said first light scanner and said second light scanner comprises a light switch.

9. A diagnostic device as claimed in claim 8, in which said light source comprises a semiconductor laser diode.

10. A diagnostic device as claimed in claim 1, in which a wavelength of said first wavelength component and said second wavelength component of said measuring light is in a range from 0.5 μm to 0.9 μm.

11. A diagnostic device as claimed in claim 10, in which said first light scanner and said second light scanner comprises a light switch.

12. A diagnostic device as claimed in claim 11, in which said light source comprises a semiconductor laser diode.

13. A diagnostic device as claimed in claim 10, in which said light source comprises a semiconductor laser diode.

14. A diagnostic device as claimed in claim 1, in which said first light scanner and said second light scanner comprises a light switch.

15. A diagnostic device as claimed in claim 14, in which said light source comprises a semiconductor laser diode.

16. A diagnostic device as claimed in claim 1, in which said light source comprises a semiconductor laser diode.

* * * * *